(12) United States Patent
Sone

(10) Patent No.: US 6,799,135 B2
(45) Date of Patent: Sep. 28, 2004

(54) USER FRIENDLY ANALYSIS SYSTEM

(75) Inventor: Yuuya Sone, Chiba (JP)

(73) Assignee: SII NanoTechnology Inc., Chiba (JP)

( * ) Notice: Subject to any disclaimer, the term of this patent is extended or adjusted under 35 U.S.C. 154(b) by 0 days.

(21) Appl. No.: 10/055,316

(22) Filed: Jan. 23, 2002

(65) Prior Publication Data

US 2002/0116692 A1 Aug. 22, 2002

(30) Foreign Application Priority Data

Jan. 29, 2001 (JP) ........................................ 2001-020562

(51) Int. Cl.[7] .............................. G01D 1/00; G06F 15/00
(52) U.S. Cl. ..................................................... 702/127
(58) Field of Search .......................... 702/127; 345/200, 345/762, 765, 804

(56) References Cited

U.S. PATENT DOCUMENTS

| | | | | |
|---|---|---|---|---|
| 5,473,536 A | * | 12/1995 | Wimmer ...................... 700/90 |
| 5,592,603 A | * | 1/1997 | Arato et al. ................. 345/762 |
| 5,609,770 A | * | 3/1997 | Zimmerman et al. ........ 210/739 |
| 5,764,546 A | * | 6/1998 | Bryant et al. ................ 702/108 |
| 5,833,623 A | * | 11/1998 | Mann et al. ................. 600/523 |
| 5,963,884 A | * | 10/1999 | Billington et al. ............ 702/56 |
| 6,063,030 A | * | 5/2000 | Vara et al. ................... 600/437 |
| 6,234,689 B1 | * | 5/2001 | Rohrbaugh et al. ......... 717/162 |
| 6,304,851 B1 | * | 10/2001 | Kmack et al. ................ 705/11 |
| 6,489,168 B1 | * | 12/2002 | Wang et al. ................... 436/37 |
| 6,507,842 B1 | * | 1/2003 | Grey et al. ..................... 707/5 |
| 6,522,345 B1 | * | 2/2003 | Alexander .................. 345/863 |

* cited by examiner

Primary Examiner—John Bartow
Assistant Examiner—Demetrius Pretlow
(74) Attorney, Agent, or Firm—Adams & Wilks

(57) ABSTRACT

An analyzer system of the present invention is capable of customizing arbitrary setting of display/non-display input possible/input impossible setting for items used in condition setting or parameter input in a user interface such as a dialog box one at a time, and storing customized conditions for each user, and is capable of restoring setting conditions desired by each user as a result of the user reading out the stored information at the time of use.

18 Claims, 4 Drawing Sheets

FIG.5

|  | STEP | 1 | 2 | 3 | 4 | END STEP | 1 |
|---|---|---|---|---|---|---|---|
|  |  |  |  |  |  | 5 |  |
| START TEMPERATURE |  | ☐ | ☐ | ☐ | ☐ | ☐ |  |
| LIMIT TEMPERATURE |  | ☐ | ☐ | ☐ | ☐ | ☐ |  |
| RATE OF TEMPERATURE RISE |  |  | ☐ | ☐ | ☐ | ☐ |  |
| SAMPLING INTERVAL |  | ☐ | ☐ | ☐ | ☐ | ☐ |  |

FIG.6

| STEP | 1 |
|---|---|
| START TEMPERATURE | ☐ |
| LIMIT TEMPERATURE | ☐ |

USER FRIENDLY ANALYSIS SYSTEM

BACKGROUND OF THE INVENTION

The present invention relates to improved technology in a user interface of an analysis system comprised of a computer having a function for performing various types of analysis on detection data.

In recent years, analyzers have tended to become integrated systems that not only simply detect and measure states of a sample in a prescribed environment and store and display these detected values, but are capable of implementing an assembly line approach for controlling operation of a detector by connecting to a personal computer or the like, extract the detected values to perform various data processing, allow display of data on a display screen as graphs or tables, perform analysis and finally collect together analysis results into the form of a report. These systems are not limited to being directly connected to detectors, and can also take the form of allowing systemization as an integrated analyzer for reading information that has been stored in a storage medium and connecting detectors in remote laboratories using communication means etc. Specifically, this type of analyzer is constructed as a system comprising hardware such as detectors, a computer, input operation means and a display, and software for controlling the detectors and performing analysis of measured data. The majority of functions used in this type of analyzer, from initial detection to the final creation of a report, except for some operations such as placing a sample in the analyzer, are carried out through computer operation. Accordingly, in order to make the analysis functions carried out using computer operation easy, a comprehensive user interface is extremely important Unfortunately, this type of analyzer is generally expensive and can not really be used for personal use such as with an ordinary personal computer, and depending on the frequency of use may be shared among a number of workplaces and a number of functions. For example, a thermal analyzer is required in order to study thermal behavior, but for an analyzer that does not have that high a rate of usage it is often the case that only one device is installed in the analysis department of a company. This type of analyzer is required to be applied to a wide range of uses, due to the fact that it will be shared by a lot of workplaces and types of industry. For this reason, an analyzer inevitably becomes a multi-function type.

Basically, analyzers require a lot of parameters when carrying out control of the device or analysis of data. The number of these parameters is increased further when the analyzer is made multi-functional, which in turn complicates the user interface. For example, in a thermal analyzer a large number of parameters are required in a temperature program for controlling temperature. For example, regarding departments carrying out instruction and development of analytical methods, since it is desired to attain maximum device performance, an environment in which it is possible to freely set a lot of parameters in small stages is desirable, but regarding sections that only carry out determined fixed analysis setting and display of parameters that do not need to be changed is only additional troublesome display, and in a situation where it is desired to set and display with a minimum of requirements, those requirements change depending on the type of industry.

Also, since changing of temporarily set parameters by other people must be reset for the next operation, there is a need to be able to prevent changing of settings. Conventional analyzers allow customization of menu structures, and moreover it is common to be able to hold only one customized condition for one program, and it was often the case that it was not possible to deal with these varying needs. There are currently no analyzers capable of subtle settings for each user (function) in a user interface such as dialog boxes (settings windows displayed during command selection).

SUMMARY OF THE INVENTION

The advantage of the present invention is to provide an analyzer enabling the setting of a number of parameters and can also handle display of only required minimum settings, and which further, by handling prevention of change of setting parameters, gives good operability and usability for all users.

An analyzer of the present invention is capable of customizing arbitrary setting of display/non-display input possible/input impossible setting for items used in condition setting or parameter input one at a time in a user interface such as a dialog box, and storing customized conditions for each user, and is capable of returning setting conditions desired by each user by the user reading out the stored information at the time of use.

BRIEF DESCRIPTION OF THE DRAWINGS

FIG. 5 is a drawing for describing a non-display selection operation in the temperature program setting window in the system of the present invention.

FIG. 6 is a drawing showing an example of a customized temperature program setting window in a system of the present invention.

DETAILED DESCRIPTION OF THE INVENTION

A user compatible analysis system of the present invention will be described using an example of the case of application to a differential scanning calorimeter (DSC), being a typical thermal analysis measurement method. Before commencement of measurement, the user interface is first of all customized.

[Operation 1] (Launch Measurement Software.)

Figure 1:
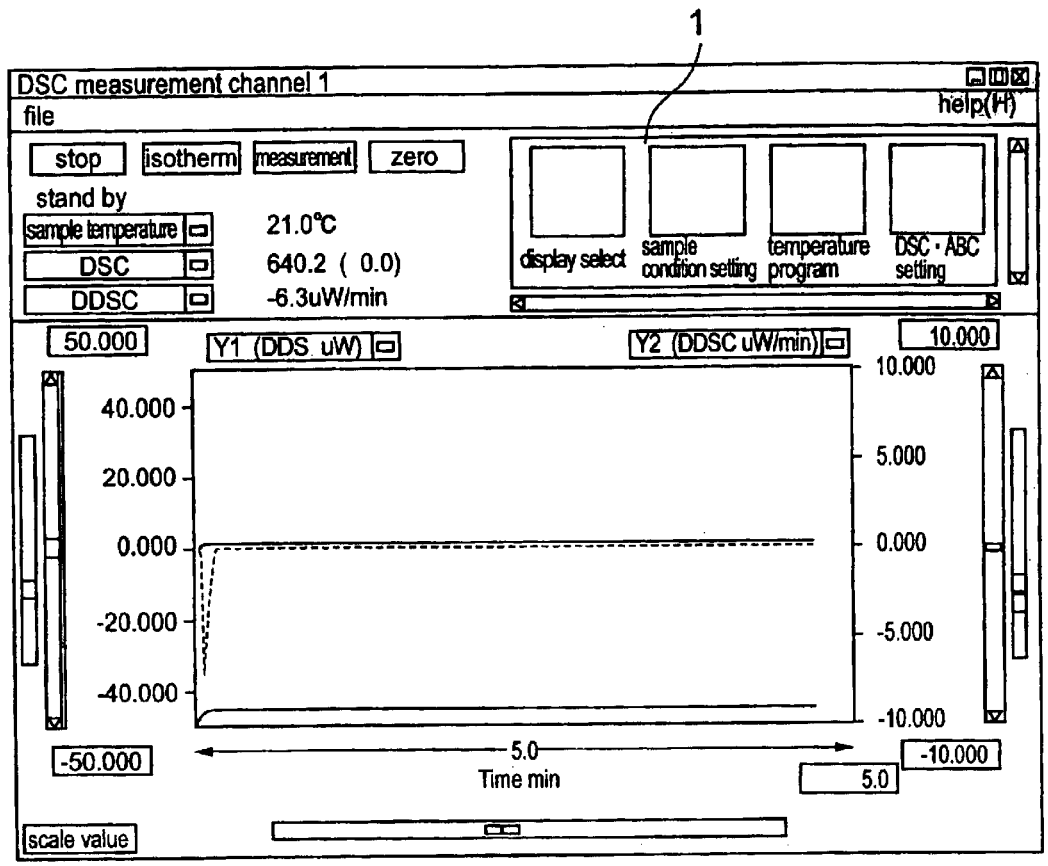
FIG. 1 is a drawing showing an example of a measurement main window in a system of the present invention.

If a switch of the analyzer is turned ON, the measurement software is launched to display a DSC measurement screen as a first display as shown in FIG. 1. Icon buttons 1 for display selection, sample condition setting, temperature program and DSC/ABC setting (constant settings for compensation of temperature drift and thermal capacity drift of the measurement device) are displayed on the screen.

[Operation 2] (Open Temperature Program Setting Window.)

Figure 2:
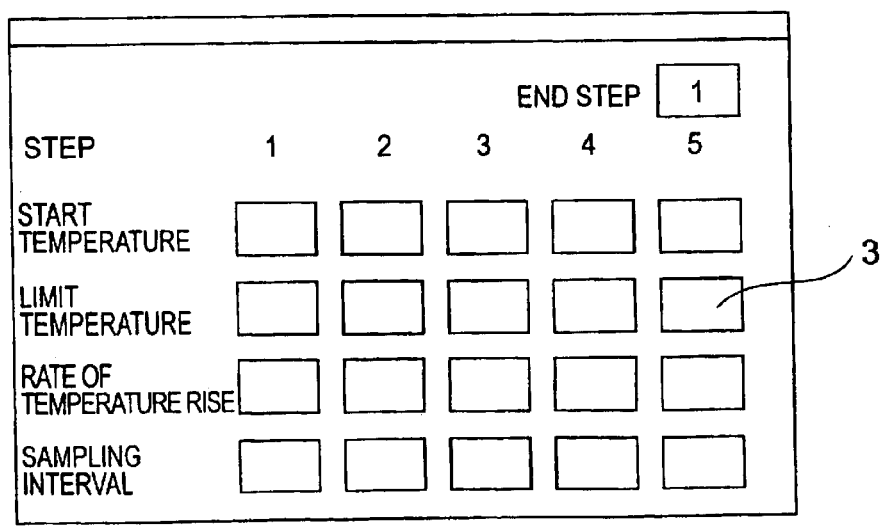
FIG. 2 is a drawing showing an example of a temperature program setting window in a system of the present invention.

If a temperature program button among the displayed icon buttons 1 is selected with a pointing device such as a mouse, a second display such as a temperature program parameter setting window as shown in FIG. 2 is displayed, prompting the setting of four parameters, namely, start temperature, limit temperature, rate of temperature rise and sampling interval corresponding to each step.

[Operation 3] (Input Temperature Program Parameters.)

A thermal analyzer measures changes in physical properties of a sample as a function of temperature or time while causing variations in the temperature of the sample, but in order to do this a sample that is the subject of measurement is inserted into a heating furnace and control is performed so as to raise and lower the temperature within that furnace as desired for a particular period of time. A set of parameters used in this temperature control are called a temperature program. A user then moves a cursor to an entry column for each parameter that requires setting on this display screen and inputs a numerical value. Start temperature means the temperature at the commencement of measurement, limit temperature means the temperature at the end of measurement, rate of temperature rise means the speed at which temperature is increased, and sampling interval means the time interval at which data is acquired. Also, end step shows what step will be executed to from step 1, and commencement of temperature control.

[Operation 4] (Select Input Item for which Non-display is Desired.)

When a certain person carries out thermal analysis, there may be cases where rate of temperature rise is determined and it is not necessary to correct settings. In this type of case, either this input column is not necessary, or rather display of this column is troublesome. A format where only columns that require input are displayed is easy for a user to operate. The present invention has a function for, in this type of case, specifying columns that do not require input and making them non-display. A user moves a cursor 4 to a not-to-be-displayed input item 3 column for items that should not be displayed, as shown in FIG. 3, to select subjects.

[Operation 5] (Right Click of the Mouse to Cause Display of Pop-up Menu.)

Figures 3, 4:
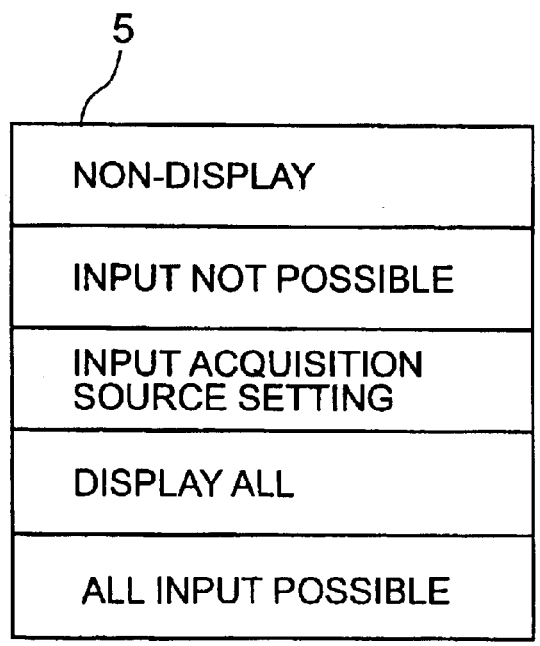
FIG. 3 is a drawing for describing a subject item selection operation in the temperature program setting window in the system of the present invention.
FIG. 4 is a drawing showing a pop-up menu used in operations in the temperature program setting window in the system of the present invention.

At the point where the cursor 4 is moved to the not-to-be-displayed input item 3 column and subjects are selected, with the present invention, a third display such as a pop-up menu 5 as shown in FIG. 4 is caused to be displayed by operation of pointing device, such as right-clicking a mouse.

The content of the menu includes 5 items of: non-display, input not possible, setting input acquisition source, display all and all input possible.

[Operation 6] (Select 'Non-display' in the Pop-up Menu.)

If the user carries out a pointing device operation such as placing a pointing arrow at a position of 'non-display' in the pop-up menu 5 and left clicking the mouse, the column for input items 3 that were initially selected is made non-display and removed from the screen, as shown in FIG. 5. If there are other items that do not require a user to change settings, such as sampling interval, [Operation 4] to [operation 6] are repeated for these items to make them non-display. Further, if this user's task only involves carrying out temperature control of step 1, that task will be made much easier if input columns for other steps are also made non-display. In this case, it is troublesome to repeat [operation 4] to [operation 6] one by one for each of the entry columns of the numerous steps. In this type of case, characters of the steps are grouped together using a method such as dragging to make them reverse video, and it is then possible to make the parameters of those steps non-display collectively. Further, in this case, since setting is unnecessary not only for step 2 but up to step 5, if display for step 2 to step 5 is carried out by collectively dragging and performing [operation 5] and [operation 6], then as shown in FIG. 6 only parameter input item columns that a user is required to input are displayed on the screen.

[Operation 7] (Close Temperature Program Setting Window.)

Customization of the user interface as described above is carried out, and this temperature program setting window is closed.

[Operation 8] (Press Setting Button to Commence Measurement, Execute Measurement.)

If the temperature program setting window is closed, the DSC measurement screen shown in FIG. 1 is displayed again. If the user then clicks on the measurement button on the screen, the analyzer enters measurement mode, measurement commences in accordance with the set temperature program to carry out specified temperature control, detection data at specified time intervals is acquired and measurement is completed.

[Operation 9] (User Opens Temperature Program Setting Window Again to Carry Out Second Measurement.)

If the user opens the temperature program setting window again in order to carry out a second measurement, the screen shown in FIG. 2 is not displayed, but instead the screen with the customized non-display setting shown in FIG. 6 is displayed. It is possible for the user to complete the temperature program setting by simply inputting values for the displayed items. It is possible to carry out the temperature program setting reliably and simply with no omission of input.

Next, a procedure for returning the setting window that has been customized with the previous sequence of operations to its original state will be described.

[Operation 1] (Launch Measurement Software.)

As with the previous operation, if a switch of the analyzer is turned ON, the measurement software is launched and the DSC measurement screen as in FIG. 1 is displayed.

[Operation 2] (Open Temperature Program Setting Window.)

Similarly, temperature program among the displayed icon buttons 1 is selected with a pointing device such as a mouse, and a temperature program parameter setting window is displayed, but this time it is not the screen as shown in FIG. 2, but the customized non-display setting screen shown in FIG. 6 that is displayed. Here, if measurement will be carried out with the same conditions, this state is desirable, but in the case where setting is also required for other parameters that are not being displayed this display is inconvenient.

[Operation 3] (Right Click of the Mouse to Cause Display of Pop-up Menu.)

The user right clicks the mouse to cause display of the pop-up menu 5 as shown in FIG. 4.

[Operation 4] (Selection of Item 'Display All' from the Menu Using an Arrow.)

The menu contains five items, namely: non-display, input possible, input acquisition source setting, display all, and all input possible, but in this case the item 'display all' is selected using an arrow. With the present invention, the structure is such that when these operations are carried out non-display is cancelled and the temperature program setting window screen of FIG. 2 is returned to.

[Operation 5] (Select Item 'All Input Possible' from the Menu Using Arrow.)

Even if all non-displays are cancelled and the column for all input items 3 is displayed, in the event that there is an input item column previously set to input not possible, that state is not cancelled. In this case, with the present invention, by selecting item 'all input possible' in the pop-up menu 5 using an arrow, the input possible state is returned to even with an input column that was previously set to input not possible. It is also possible to have a structure where, when a state where a user can input all input item columns is returned to, by selecting the item 'all input possible' instead of 'display all' from the pop-up menu 5 using an arrow in operation 4, a display all and all input possible state is directly entered. Generally, when entering an all input possible state, it is more convenient to display all input item columns, and so this structure is more useful.

Making items in the program non-display has the effect that that there is no need for a user to set these parameters at the time of measurement, but this does not mean that those parameters are not actually required or that they are determined by a user, but that they have already been decided. Parameter values that have already been decided are sometime input as fixed values and thereafter put into an input not possible state, but it is also possible to acquire the values from a file. This operation will be described next.

[Operation 1] Launch measurement software.
[Operation 2] Open temperature program setting window.
[Operation 3] Input parameters of temperature program.
[Operation 4] Select items to be made non-display.
[Operation 5] Right click mouse to display pop-up menu.

Operations up to this point are the same as for non-display setting. Specifically, the cursor 4 is moved to input items 3 to be made non-display and the mouse right clicked or the like to open a pop-up menu. Then [Operation 6] (Select 'select source of input value acquisition' from the pop-up menu.) is performed.

Figure 7:
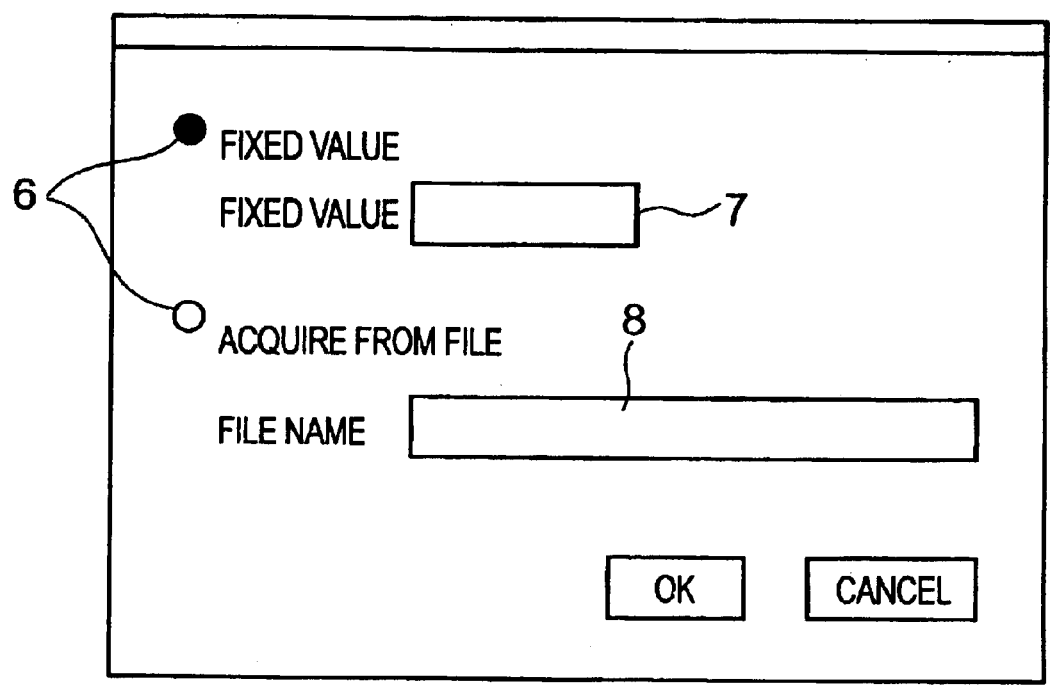
FIG. 7 is a drawing showing an example of a window when "set source of input value acquisition" has been selected from the pop-up menu.

Here, if 'select source of input value acquisition' is selected from the pop-up menu 5, the present invention is configured so as to open the window shown in FIG. 7.

In the event that fixed values are designated as a source of input values, then after a fixed value radio button 6 has been clicked the cursor 4 is moved to a fixed value edit box 7 and a numerical value is input.

If this is done, the input values are used as parameters once the input items 3 have been set to non-display. Also, in the event that a file is designated as the source of input values, the cursor 4 is moved to a file name edit box 8 after an acquire from file radio button 6 has been clicked, and the file name is then input.

If this is carried out, parameter values are read from the corresponding file, and the read values are used as parameters once the input items 3 have been set to non-display. This file is not limited to a directory within the analyzer itself, and it is also possible to acquire data by connecting to a remote laboratory or the like using communication means.
[Operation 7] (Close Selection Window for Input Value Acquisition Source.)

If selection of an input value source is complete, the 'OK' button in the input value acquisition source selection window is clicked and the window is closed.
[Operation 8] (Select Input Item Columns to be Made Non-display, and Reopen Pop-up Menu.)

After setting parameter values and closing the input value acquisition source selection window, the cursor 4 is once again moved to a column of an input item 3 to be made non-display, subjects selected and the pop-up menu 5 opened once more.
[Operation 9] (Select 'Non-display' from the Pop-up Menu.)

'non-display' is selected from the opened pop-up menu 5. If this is carried out, a selected input item 3 column is made non-display on the screen. Here, the input item 3 that has been made non-display uses either a fixed value or a file value that was set in [operation 6] as a parameter.

Also, if 'input not possible' has been selected from the pop-up menu 5, the present invention causes the selected input item 3 to be displayed in a "grayed out" manner, to indicate that they are in an input not allowed state. With this function, it is possible to prevent parameters that should not be changed from being changed by mistake or being overwritten by another operator.
[Operation 10] Close Temperature Program Setting Window.
[Operation 11] (Click 'Measurement' Button to Commence Measurement.)

If the temperature program setting window is closed, the DSC measurement window shown in FIG. 1 is displayed again. If the user clicks the 'measurement' button on the screen, measurement mode is entered, measurement in accordance with the set temperature program commences, specified temperature control is performed, detection data for specified time periods is acquired and measurement is completed.
[Operation 12] (User Reopens Temperature Program Setting Window in Order to Carry out Second Measurement.)

If the user reopens the temperature program setting window in order to perform a second measurement, the initial screen shown in FIG. 2 is not displayed, but instead the screen previously customized with non-display settings is displayed. It is possible for the user to complete temperature program setting by simply inputting items that have been displayed.

Next, a description will be given of storing settings for each user (or type of industry) and reading out settings, for when a plurality of users in charge of different types of industry use the same analyzer. With the present invention, if the user opens the temperature program setting window in order to perform measurement, initially the system starts up in a customized state. In the case where the user is the same as the previous user, or a person is involved in the same type of industry, this is extremely useful, but in the event that there are users utilizing the analyzers for completely different tasks, this setting needs to be performed again for each user. Naturally, the initially described setting changes are possible, but since the same settings will also be used the next time they are used, redoing the settings each time will not be efficient. With the present invention, a function is provided making it possible to save different user interface settings in a file for each user, and at the time of starting up the analyzer, to select settings for the operator at that time.

Specifically, with the present invention, if 'File (F)' is selected from the menu bar at the time the analyzer is started up a pull down menu is opened, and if 'open' is selected from this menu a window opens, and a field indicating selection of a file directory, a list of file names stored in that directory and a currently selected file name are displayed. The content of the window displayed at that time is the settings used by the immediately previous operator, which means that if the same settings are to be used, if 'OK' is clicked the interface proceeds to the next step with the current settings saved as they are, but in the case of a different task, 'OK' is clicked after selection of an appropriate settings file from a list being displayed, and once the appropriate file is selected the analyzer is updated to settings in accordance with the setting information stored in that file.

Accordingly, with the present invention, settings previously stored in a setting file can be immediately set into the analyzer without the need to re-input revised settings. Even if another user changes various settings, it is possible to restore to one's own settings without being affected at all. When carrying out new setting using the functions of the present invention, if 'file (F)' is selected from the menu bar and 'name and save' is designated from the pull down menu, those settings are saved in a setting file and used in the future when carrying out tasks with the same settings. In the above description, various selections and specific instructions such as menus have been performed through the action of a mouse, but the present invention is not limited in this respect and it goes without saying that it is also possible to use various pointing devices.

An analysis system of the present invention built into an analyzer or connected to an analyzer comprises one or a plurality of software programs for controlling the analyzer or analyzing measurement data output from the analyzer, and is provided with a user interface for receiving input of parameters for performing control of the analyzer or analysis of measurement data, means enabling arbitrary customization of the user interface and means enabling saving/restoration of customized interface states, which means that when performing a second measurement or when starting up the next time it is possible to perform straight away without the need to modify settings.

In the customizing means, through arbitrary display of individual input components on a user interface such as a dialog box, or alternatively by endowing the system with a function to be able to make items non-display, it is possible to allow display of only items that need to be input by a user, thus preventing erroneous operations through clear screen display.

Also, with the analysis system of the present invention, in the customizing means, through arbitrary display of individual input components on a user interface such as a dialog box, or alternatively by endowing the system with a function to be able to make input not possible, since it is possible to make only items that need to be input by a user input possible, it is possible to prevent erroneous operation with respect to items that do not requires setting changes, thus promoting error free operation. In the customization means of the analysis system of the present invention, when components involved in input of parameters are made non-display, by providing a function to enable acquisition of information from locations where input values have been arbitrarily designated, it is possible to eliminate the task of a user re-doing updated settings and immediately take in information in an arbitrary directory in a state where general settings that are made non-display are saved without change.

Also, in the means for saving/restoring customized states of the analysis system of the present invention, when the system is used by a plurality of users, by providing a function to enable saving/restoration of customized states corresponding to respective users it is possible for a number of users to use a single analyzer as if it were a dedicated system without settings for each user affecting each other.

What is claimed is:

1. A user interface for a sample analyzer having a computer, comprising: a first display having one or more user-selectable control items for controlling a sample analysis procedure and one or more user-selectable analysis items for controlling analysis of measurement results; a second display generated in response to user selection of a control item from the first display for requesting user input of parameters for use in controlling the sample analysis procedure; customization means for performing customization of the second display by generating a third display having user-selectable options for the parameters; and customized state storing/restoring means for saving and restoring customized states of the second display.

2. An analysis system, built into an analyzer or connected to an analyzer, containing one or more software programs for use in controlling the analyzer or analyzing measurement data output from the analyzer, comprising: a user interface for displaying items for which parameters are input by a user for use in controlling an analysis procedure performed by the analyzer or controlling analysis of measurement data; customization means for performing customization of the user interface; and customized state storing/restoring means for saving and restoring customized states of the user interface; wherein the customization means generates a dialog box containing user-selectable options that permit user-selection of whether or not respective items are to be displayed; and wherein the customization means obtains a value of a respective parameter from a designated location when user input of the respective parameter is not permitted.

3. An analysis system, built into an analyzer or connected to an analyzer, containing one or more software programs for use in controlling the analyzer or analyzing measurement data output from the analyzer, comprising: a user interface for receiving input of parameters for use in controlling an analysis procedure performed by the analyzer or controlling analysis of measurement data; customization means for performing customization of the user interface; and customized state storing/restoring means for saving and restoring customized states of the user interface; wherein the customization means generates a dialog box that permits user-selection of whether or not user input of respective parameters is possible.

4. An analysis system according to claim 2; wherein the customization means obtains a value of a respective parameter from a designated location when an item corresponding to the respective parameter is set to not be displayed in the second display.

5. An analysis system according to claim 2; wherein the customized state storing/restoring means saves and restores customized states matched to individual users when the analyzer is utilized by a plurality of users.

6. An analysis system according to claim 2; wherein the customization means generates a dialog box containing options that permit user-selection of whether or not respective items are to be displayed.

7. An analysis system according to claim 2; wherein the analyzer is a differential scanning calorimeter.

8. A user interface for a sample analyzer according to claim 3; wherein the customized state storing-restoring means saves and restores customized states matched to individual users when the sample analyzer is utilized by a plurality of users.

9. An analysis system according to claim 3; wherein the analyzer is a differential scanning calorimeter.

10. A user interface for a sample analyzer according to claim 1; wherein the customization means generates a dialog box as the third display, and the user-selectable options contained in the dialog box permit user-selection of whether or not user input of respective parameters is possible in the second display.

11. A user interface for a sample analyzer according to claim 1; wherein the customization means generates a dialog box as the third display, and the user-selectable options contained in the dialog box permit user-selection of whether or not respective parameters are to be displayed in the second display.

12. A user interface for a sample analyzer according to claim 11; wherein the customization means obtains a value of a respective parameter from a designated location when the respective parameter is set to not be displayed in the second display.

13. A user interface for a sample analyzer according to claim 1; wherein the customization means obtains a value of a respective parameter from a designated location when the respective parameter is set to not be displayed in the second display.

14. A user interface for a sample analyzer according to claim 1; wherein the customized state storing/restoring means saves and restores customized states matched to individual users when the sample analyzer is utilized by a plurality of users.

15. A user interface for a sample analyzer according to claim 1; wherein the sample analyzer is a differential scanning calorimeter.

16. A user interface for a sample analyzer according to claim 1; wherein the first display contains an image of sample characteristics.

17. A user interface for a sample analyzer according to claim 16; wherein the sample analyzer is a differential scanning calorimeter.

18. A user interface for a sample analyzer according to claim 17; wherein the image of sample characteristics is a data curve.

* * * * *